United States Patent [19]

Cox

[11] 4,411,268

[45] Oct. 25, 1983

[54] MUSCLE STIMULATOR

[75] Inventor: James A. Cox, Sewell, N.J.

[73] Assignee: Medtronic, Inc., Minneapolis, Minn.

[21] Appl. No.: 347,514

[22] Filed: Feb. 10, 1982

[51] Int. Cl.³ .............................................. A61N 1/36
[52] U.S. Cl. ............................... 128/421; 128/419 PG
[58] Field of Search ................ 128/419 PG, 421, 422, 128/423 R, 423 V

[56] References Cited

U.S. PATENT DOCUMENTS

| | | | |
|---|---|---|---|
| 3,344,792 | 10/1967 | Offner et al. | 128/419 R |
| 3,364,929 | 1/1968 | Ide et al. | 128/419 R |
| 3,433,228 | 3/1969 | Keller, Jr. | 128/419 PG |
| 3,851,651 | 12/1974 | Icenbice, Jr. | 128/422 |
| 3,933,147 | 1/1976 | Duvall | 128/421 |
| 3,983,881 | 10/1976 | Wickham | 128/422 |
| 4,157,087 | 6/1979 | Miller et al. | 128/423 R |

*Primary Examiner*—William E. Kamm
*Attorney, Agent, or Firm*—Schroeder, Siegfried, Vidas & Arrett

[57] ABSTRACT

A system for inducing a desired functional contraction in muscle tissue while conditioning the contractile properties of that tissue for the desired functional contraction. Pacing stimulation signals are generated having parameters established by a desired functional contraction of particular muscle tissue, the signals being applied to the body to initiate the contraction. A conditioning stimulation signal is also generated having parameters established by the desired functional contraction and applied to the body to condition the contractile properties of the particular muscle tissue. The conditioning stimulation signal may transform the contractile properties of the tissue or maintain those properties, which may also include the responsiveness of the tissue to pacing stimulation signals. In a preferred embodiment, the conditioning stimulation signal is a signal having a frequency from about 1.5 hertz to about 20 hertz and most preferably about 10 hertz. In another preferred embodiment, the conditioning stimulation signal has a frequency from about 80 hertz to 2,000 hertz and most preferably about 100 hertz. In all preferred embodiments, the signal may be continuous or discontinuous.

36 Claims, 1 Drawing Figure

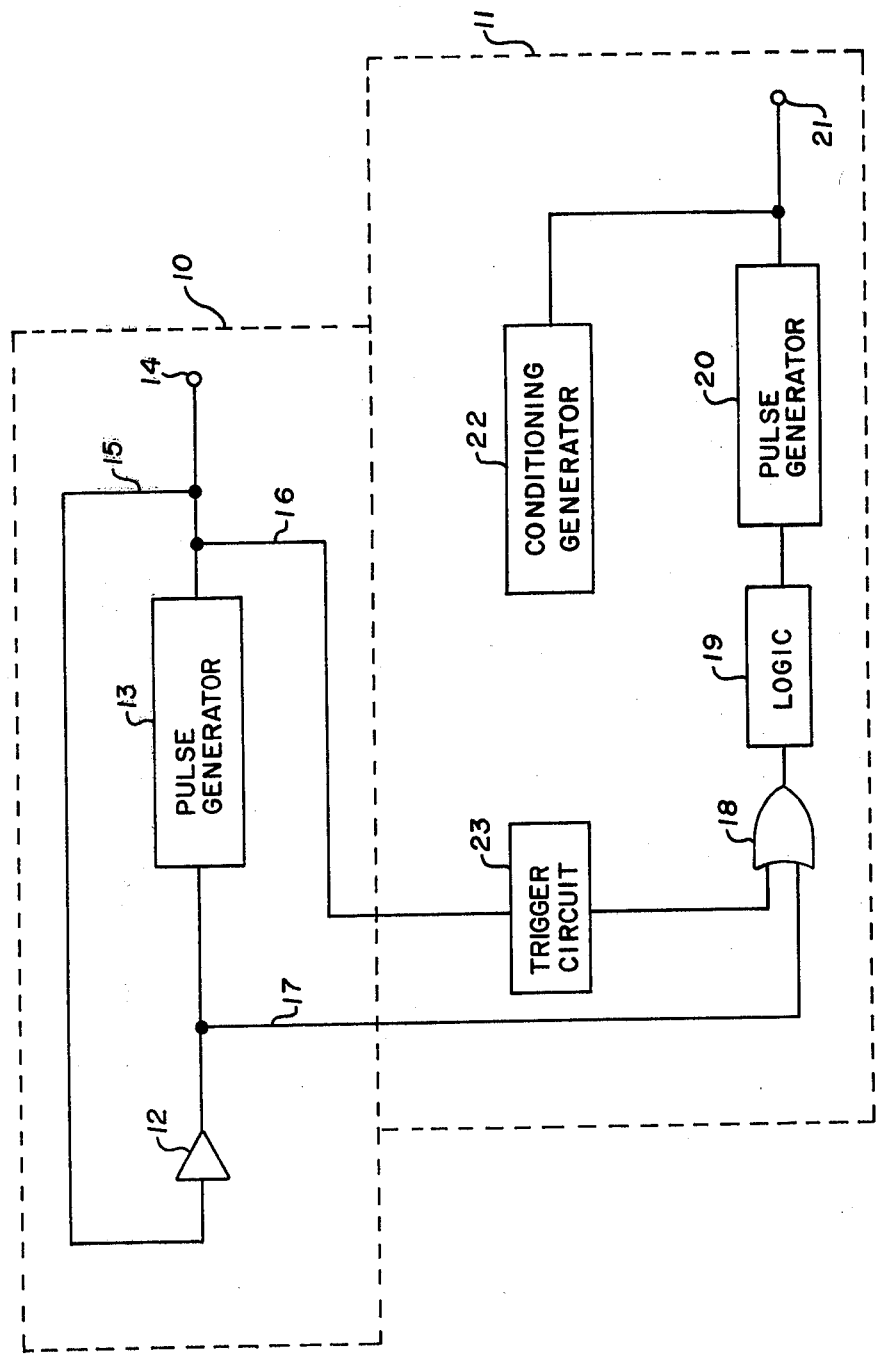

MUSCLE STIMULATOR

DESCRIPTION

BACKGROUND OF PRIOR ART

Induced muscle contraction through the application of electrical stimulation is well known to the prior art. An example of such a contraction is that induced in the heart by the well-known cardiac pacemaker. Other induced muscle contractions also have proven medically beneficial.

Some muscle dysfunctions and insufficiencies are not adequately or appropriately addressed by contraction inducing electrical stimulation. For example, the muscle tissue may not be adequately responsive to stimulation energy or may require too high an energy threshold for practical contraction inducement. In such instances, a surgical therapy would be a useful alternative, the replacement of non-functioning myocardial tissue with contractile tissue, for example. Ideally, such a tissue graft should have the potential for growth and differentiation and be autogenous so as to overcome the problems associated with tissue rejection. Another condition that could be addressed through a graft of contractile tissue is a congenitally hypoplastic heart, or a portion thereof. Numerous other examples of muscle contraction dysfunctions and insufficiencies that could be addressed by the grafting of contractile tissue will be apparent to those familiar with muscle physiology.

It is unlikely that a muscle graft, as described above, will contract in response to the same processes that induce a normal contraction in the surrounding tissue. Accordingly, it may be necessary to provide a system that will induce a contraction in the grafted tissue. Further, the tissues conveniently available may be of the wrong response type, the differentiation of muscle tissue between fast and slow—often referred to as fast twitch and slow twitch, respectively—being well known. For example, in a replacement of myocardial tissue or the surgical therapy for congenitally hypoplastic portions of the heart discussed above, it appears most convenient to use diaphragm tissue for the tissue graft. However, diaphragm muscle tissue is a fast muscle while myocardial tissue is a slow muscle. Thus, a diaphragm graft on the heart can be expected to fatigue if it retains its fast muscle character. Accordingly, in conjunction with providing a pacing system for a muscle graft, it is desirable that that system have the capability of conditioning the muscle graft to transform it to the desired muscle response type and/or maintain a desired muscle response type.

BRIEF SUMMARY OF INVENTION

The present invention provides a system for inducing a desired functional contraction in muscle tissue while conditioning the contractile properties of that tissue for the desired functional contraction. The system provides pacing stimulation signals having parameters established by the desired functional contraction of particular muscle tissue, the stimulation signals being applied to the body to initiate the desired functional contraction of the tissue in question. The system also provides a conditioning stimulation signal whose parameters are established by the desired functional contraction, the conditioning signals also being applied to the body for conditioning the contractile properties of the tissue in question. Thus, the system of the present invention induces a desired contraction in particular muscle tissue while conditioning that tissue to the type of contraction it is desired to induce. The conditioning may include a transforming of the tissue from one response type to another or the maintenance of the tissue as a certain response type.

In the practice of the present invention, when it is desired to condition muscle tissue as slow tissue, either by transformation from fast tissue or for maintenance as slow tissue, the conditioning stimulation signal has a relatively low frequency preferably within the range from about 1.5 hertz to about 20 hertz. Most preferably, the slow tissue conditioning stimulation signal will have a frequency of about 10 hertz. When it is desired to condition fast tissue, either by transformation from slow tissue or maintenance as fast tissue, the conditioning stimulation signal has a relatively high frequency, preferably in the range from about 80 hertz to about 2,000 hertz. Most preferably, the fast tissue conditioning stimulation signal will have a frequency of about 100 hertz. It is known that conditioning stimulation signals having the stated relative frequencies will accomplish the desired conditioning when the energy level of the signal is above the capture threshold level of the muscle in question. It is believed that the same results will be obtained with conditioning stimulation signals below the threshold level. Further, the conditioning may be for the purpose of making the tissue more responsive to a pacing stimulation signal only or in addition to a conditioning of muscle type. The conditioning signal may be applied continuously or discontinuously. Further, the pacing signal may be timed relative to the contraction of adjacent tissue, either natural or induced, to time the contraction of the tissue being conditioned in a desired relationship with the adjacent tissue.

BRIEF DESCRIPTION OF DRAWINGS

The single FIGURE illustrates, in diagrammatic form, the system of the present invention.

DETAILED DESCRIPTION OF INVENTION

For the purpose of this specification and claims, the term "threshold" means the lowest stimulation signal energy level that will result in a contraction of a muscle. "Capture" results from the application of a stimulation signal above threshold. A "functional contraction" is a muscle contraction intended to result in, or contribute to, a desired present result. Heart contraction, limb flexion, diaphragm action, etc., are among the many functional contractions that occur in the body. Thus, a functional contraction may be the contraction of a muscle in its entirety or a muscle graft, the latter contributing to the functional contraction of the former.

The term "pacing stimulation" is intended to embrace all artificial electrical stimulation that is applied to the body to initiate a functional contraction. In the context of the heart, such pacing stimulation is in the form of a series of pacing pulses each initiating a heart contraction. Thus, each pacing pulse in the pulse series can be thought of as being applied acutely although the therapy is applied chronically. In contrast to pacing stimulation, "conditioning stimulation" is intended to embrace all artificial electrical stimulation applied to transform or maintain particular contractile properties of muscle. Although a conditioning stimulation signal is typically in the form as a series of pulses, within the parameters set forth below, the individual pulses are not intended to induce a functional contraction. Instead, the compound effect of the pulses forming the conditioning stimulation energy pulse train are the intended result. Accordingly, conditioning stimulation can be thought of as being applied chronically.

As noted herein, the use of pacing stimulation to induce a functional contraction is well known. The parameters of the pacing stimulation are established by the desired functional contraction of the particular muscle tissue that it is intended to contract. The establishment of these parameters are within the skill of one ordinarily skilled in the art. Typically, pacing stimulation is applied directly to the muscle that it is desired to stimulate although nerve stimulation has also been employed to induce muscle contraction.

In some instances, pacing stimulation is inadequate or inappropriate to overcome muscle contractile disfunctions or insufficiencies. Examples of these instances include muscular atrophy and disease processes due to a breakdown in neural activity and function, or inadequate muscle tissue. An example of the latter is a congenitally hypoplastic condition of the heart, or a portion thereof. A surgical therapy for such a condition would ideally involve an enlargement with contractile, autogenous tissue having the potential for growth while overcoming problems associated with tissue rejection. A convenient source for such tissue is the diaphragm. However, the diaphragm is a fast muscle, as opposed to the slow muscle type of the myocardium, and is thus subject to muscle fatigue. Further, a graft of diaphragm tissue on the heart does not respond to the propagation of a depolarization wave, of natural or artificial origin, as does the natural tissue adjacent to it. Thus, to maximize the benefits from such a graft, the graft must not only be induced to contract through the application of pacing stimulation but the graft tissue, itself, should be conditioned as by transforming it from a fast muscle type to a slow muscle type. The latter is accomplished through the application of conditioning stimulation which, after transformation, may be usefully applied to maintain the tissue in the transformed state.

The ability to transform muscle type has been known for some time. One manner in which it has been accomplished is the maintenance of laboratory animals in hypergravity conditions for extended periods of time. However, the fact that the differentiation of muscle into fast or slow types is determined largely by neural influence has been established by cross-reinnervation experiments. Early, it was thought that such a differentiation was induced by neurotropic factors. More recently, however, it has become accepted that muscular differentiation as well as transformation of muscle type are the result of muscle activity. T. Lomo, R. H. Westgaard and L. Engebretsen, "Different Stimulation Patterns Affect Contractile Properties of Denervated Rat Soleus Muscles," *Plasticity of Muscle* (Walter de Gruyter and Co., 1980), Pps. 297-309.

The present invention provides a system whereby the ability to transform muscle type is augmented by the ability to induce a contraction in that muscle such that the muscle results in or contributes to a functional contraction. The system has particular application in the instance of a graft of one muscle type on muscle tissue of another type, the graft being intended to contribute to the result of the functional contraction of the muscle on which it is grafted. This has special relevance in the instance of a graft of diaphragm contractile tissue on the heart, and in particular on the ventrical. A preferred embodiment of the present invention will be described within this context.

Referring now to the single figure, there are illustrated two boxes formed of broken lines 10 and 11. The elements within box 10 form a conventional cardiac pacemaker of the demand type including a sense amplifier 12 and pulse generator 13, the output of the pulse generator 13 being applied to an output terminal 14 and to a line 15 connected to the input of the sense amplifier 12. The output of the pulse generator 13 is also applied to a line 16 while the output of the sense amplifier 12 is also applied to a line 17, both to be described more fully below. In operation, the sensing of natural heart activity will result in a signal at the terminal 14 and an input to the sense amplifier 12. The sense amplifier 12, in response to the sensing of natural heart activity, will reset the timing circuitry of the pulse generator 12 to prevent the delivery of a pacing stimulation signal for a predetermined period of time. Should natural heart activity be sensed again within that predetermined time period, the pulse generator 13 will again be reset and deliver no output. This will continue until such time as natural heart activity is not sensed within the escape interval of the pulse generator 13 at which time the pulse generator 13 will deliver a pacing stimulation signal to the terminal 14 and, accordingly, to the heart via a lead system of known design. As stated above, this operation is conventional and is noted here briefly for the sake of clarity.

Line 17 and line 16, via a trigger circuit 23, are connected to the inputs of an OR gate whose output is connected to logic circuitry 19. Logic circuitry 19 is connected to control a pulse generator 20 whose output is connected to a terminal 21. A conditioning signal generator 22 is also connected to the terminal 21, the terminal 21 being adapted for connection to a lead system to deliver signals appearing at the terminal 21 to a muscle which it is desired to condition and pace or to a nerve innervating such muscle.

Pulse generator 20 is of the type that will generate pacing stimulation signals and deliver them to the terminal 21. Parameters of the pacing stimulation signals are dependent on the desired functional contraction of the particular muscle tissue it is intended to stimulate, and therefore, the muscle tissue itself. For example, if myocardial tissue is being stimulated to induce a contraction, the parameters would be those of a typical cardiac pacemaker. For other muscle tissue, establishment of the output parameters of the pulse generator 20 are well within the skill of one ordinarily skilled in the art. For example, in the event that the tissue being stimulated is contractile diaphragm tissue grafted to the heart, the parameters will be established in accordance with the requirements of the diaphragm tissue, as opposed to the adjacent myocardial tissue. Of course, as the muscle type of the grafted tissue transforms, the parameters may change requiring a reprogramming of the pulse generator 20, as will be described more completely below.

Conditioning generator 22 generates a conditioning stimulation signal whose parameters are established by the desired functional contraction induced by the pacing stimulation signals from pulse generator 20. That is, in the event that the functional contraction is one ordinarily undergone by slow muscle tissue, the conditioning stimulation signal will be one that will condition that tissue, either by transformation from fast tissue to slow tissue or by maintenance as slow tissue. Conversely, in the event that the tissue is a slow tissue while the desired functional contraction is one normally undergone by fast tissue, the conditioning stimulation signal will be one to condition the tissue, either by transformation or maintenance, as fast tissue. In this manner, the tissue in question will be paced and conditioned to accomplish or contribute to the desired functional contraction while being transformed or maintained to better accomplish or contribute to that contraction.

The conditioning generator 22 and pulse generator 20 may operate as described above without an input from logic circuit 19. For example, it has been found that an overall cardiac depolarization can result from a pacing stimulation signal applied to a muscle tissue grafted thereto. Thus, particularly if the pulse generator 20 is operating asynchronously, effective capture of the heart can be established by pacing the tissue graft while conditioning that graft to better contribute to the overall heart contraction.

It has also been found that a graft of diaphragm contractile tissue on the myocardium will not contract in response to a depolarization of adjacent myocardial tissue. Thus, if the graft is to contribute to the overall cardiac contraction, pulse generator 20 must capture of the graft to induce a contraction. Obviously, if this contraction is to contribute to the overall cardiac output, the graft contraction must be in proper time sequence to the depolarization of the adjacent myocardial tissue. This can be accomplished in the embodiment of the figure wherein the terminal 14 is connected to sense natural depolarization of myocardial tissue with the signals sensed at the terminal 14 being transmitted via the lines 15 to the sense amplifier 12, the output of sense amplifier 12 being applied via line 17 to the OR gate 18 whose output is applied to the logic 19. In this instance, logic 19 need be nothing more than a delay circuit that triggers the pulse generator 20 with the delay being established by the relative desired time interval between a depolarization of the tissue monitored at terminal 14 and the tissue to which the output of pulse generator 20 will be applied via terminal 21. Trigger circuit 23 has a threshold set to provide an input to OR gate 18 only in response to input signals to it that approximate or exceed the amplitude of the output from pulse generator 13. Thus, signals representative of sensed natural heart activity at terminal 14 will be blocked by the trigger circuit 23. Trigger circuit 23 may also have suitable filtering circuitry to further assure its response only in response to an output from pulse generator 13, as will be described below.

The discussion of the preceding paragraph assumes natural heart activity without an output from pulse generator 13. In the event that the heart is contracting at an acceptable rate, pulse generator 13 may be dispensed with together the line 16, trigger circuit 23 and OR gate 18 with the line 17 being connected directly to the delay logic 19. However, in the event that artificial stimulation is necessary, or it is anticipated that it will be necessary, all components illustrated in box 10 will be provided. In that instance, failure to sense natural heart activity at an adequate rate will result in an output from pulse generator 13 to the terminal 14 to initiate a heart contraction. That output will be applied to the line 16 as an input to the trigger circuit 23, the input in this instance being above the threshold of the trigger circuit 23 resulting in an input to OR gate 18 and an output from OR gate 18 as an input to logic 19. Again, logic 19 serves chiefly as a delayed trigger for pulse generator 20 to result in a proper synchronous contraction of the tissue stimulated by pulse generator 20. Of course, if pulse generator 13 is an asynchronous pulse generator, the line 15, sense amplifier 12, line 17 and OR gate 18 may be dispensed with with trigger circuit 23 being connected directly to logic 19.

As noted above, the output parameters of conditioning generator 13 are dependent upon the desired functional contraction of particular muscle tissue. It has been found that the critical parameter for any muscle tissue transformation or maintenance is the frequency of the signal. For transformation of slow tissue to fast tissue, or maintenance of fast tissue as fast tissue, the frequency range is from about 80 hertz to about 2,000 hertz and, most preferably, about 100 hertz. For fast tissue transformation to slow tissue, or maintenance of slow tissue, the frequency ranges from about 1.5 hertz to about 20 hertz and, most preferably, about 10 hertz. Amplitude and pulse width criticality has not been established. However, it is known that energy levels above the threshold of the muscle being stimulated will result in the desired transformation and maintenance. However, it is believed that energy levels below threshold will also result in the desired transformation or maintenance. Further, the threshold is dependent on the manner in which the conditioning stimulation is delivered. Successful transformation and maintenance has been established by both direct application of the conditioning stimulation signals as well as by nerve stimulation of innervated muscle tissue. The latter has a lower threshold. It is believed that both continuous and intermittent, or discontinuous, conditioning stimulation will effect the desired result.

Obviously, many modifications and variations of the present invention are possible in light of the above teachings. For example, programmable pulse generators are known to the prior art. Pulse generators 13 and 20 as well as conditioning generator 22 may employ this reprogramming technology to provide for an alteration in their output parameters, or to turn them on or off. This reprogramming might be useful on the completion of a muscle transformation that may require differing parameters in the pacing stimulation signals from pulse generator 20. Similarly, logic 19 may be externally activated or shut off or have its delay altered. Unipolar and bipolar delivery systems may be employed. Indeed, although terminals 14 and 21 are not discussed in details as such, they may be construed as including any appropriate delivery system such as lead systems known to the prior art. It is therefore to be understood that, within the scope of the appended claims, the invention may be practiced otherwise than as specifically described.

I claim:

1. A system for inducing a desired functional contraction in muscle tissue while conditioning the contracile properties of said tissue for said functional contraction which comprises:
  means for generating pacing stimulation signals having parameters established by a desired functional contraction of particular muscle tissue including means applying said pacing stimulation signals to the body for initiating said desired functional contraction of said particular muscle tissue; and
  means for generating a conditioning stimulation signal having parameters established by said desired functional contraction including means applying said conditioning stimulation signals to the body for conditioning the contractile properties of said particular muscle tissue.

2. The system of claim 1 wherein said means for conditioning comprises means for transforming the contractile properties of said particular muscle tissue.

3. The system of claim 1 wherein said means for conditioning comprises means for maintaining the contractile properties of said particular muscle tissue.

4. The system of claim 1 wherein said conditioning stimulation signal comprises a signal having a frequency from about 1.5 Hz to about 20 Hz.

5. The system of claim 4 wherein said conditioning stimulation signal comprises a continuous signal.

6. The system of claim 5 wherein said means for conditioning comprises means for transforming the contractile properties of said particular muscle tissue.

7. The system of claim 5 wherein said means for conditioning comprises means for maintaining the contractile properties of said particular muscle tissue.

8. The system of claim 4 wherein said conditioning stimulation signal comprises a discontinuous signal.

9. The system of claim 8 wherein said means for conditioning comprises means for transforming the contractile properties of said particular muscle tissue.

10. The system of claim 8 wherein said means for conditioning comprises means for maintaining the contractile properties of said particular muscle tissue.

11. The system of claim 1 wherein said conditioning stimulation signal comprises a signal having a frequency of about 10 Hz.

12. The system of claim 11 wherein said conditioning stimulation signal comprises a continuous signal.

13. The system of claim 12 wherein said means for conditioning comprises means for transforming the contractile properties of said particular muscle tissue.

14. The system of claim 12 wherein said means for conditioning comprises means for maintaining the contractile properties of said particular muscle tissue.

15. The system of claim 11 wherein said conditioning stimulation signal comprises a discontinuous signal.

16. The system of claim 15 wherein said means for conditioning comprises means for transforming the contractile properties of said particular muscle tissue.

17. The system of claim 15 wherein said means for conditioning comprises means for maintaining the contractile properties of said particular muscle tissue.

18. The system of claim 1 wherein said conditioning stimulation signal comprises a signal having a frequency from about 80 Hz to about 2000 Hz.

19. The system of claim 18 wherein said conditioning stimulation signal comprises a continuous signal.

20. The system of claim 19 wherein said means for conditioning comprises means for transforming the contractile properties of said particular muscle tissue.

21. The system of claim 19 wherein said means for conditioning comprises means for maintaining the contractile properties of said particular muscle tissue.

22. The system of claim 18 wherein said conditioning stimulation signal comprises a discontinuous signal.

23. The system of claim 22 wherein said means for conditioning comprises means for transforming the contractile properties of said particular muscle tissue.

24. The system of claim 22 wherein said means for conditioning comprises means for maintaining the contractile properties of said particular muscle tissue.

25. The system of claim 1 wherein said conditioning stimulation signal comprises a signal having a frequency of about 100 Hz.

26. The system of claim 25 wherein said conditioning stimulation signal comprises a continuous signal.

27. The system of claim 26 wherein said means for conditioning comprises means for transforming the contractile properties of said particular muscle tissue.

28. The system of claim 27 wherein said means for conditioning comprises means for maintaining the contractile properties of said particular muscle tissue.

29. The system of claim 25 wherein said conditioning stimulation signal comprises a discontinuous signal.

30. The system of claim 29 wherein said means for conditioning comprises means for transforming the contractile properties of said particular muscle tissue.

31. The system of claim 29 wherein said means for conditioning comprises means for maintaining the contractile properties of said particular muscle tissue.

32. The system of claim 1 wherein said means for conditioning comprises means applying said conditioning stimulation signal directly at the site of said particular muscle tissue.

33. The system of claim 1 wherein said particular muscle tissue comprises innervated muscle tissue, said means for conditioning comprising means applying said conditioning stimulation signal to a nerve of said particular muscle tissue.

34. The system of claim 1 wherein said means for conditioning conditions the responsiveness of said particular muscle tissue to said pacing stimulation signals.

35. The system of claim 1 further comprising means for inducing a functional contraction in muscle tissue functionally associated with said particular muscle tissue, said pacing stimulation signals generating means comprising means responsive to said functional contraction inducing means for generating said pacing stimulation signals in predetermined time relationship with the functional contraction of said functionally associated muscle tissue.

36. The system of claim 1 further comprising means for sensing a functional contraction in muscle tissue functionally associated with said particular muscle tissue, said pacing stimulation signals generating means comprising means responsive to said functional contraction sensing means for generating said pacing stimulation signals in predetermined time relationship with the functional contraction of said functionally associated muscle tissue.

* * * * *

UNITED STATES PATENT AND TRADEMARK OFFICE
CERTIFICATE OF CORRECTION

PATENT NO. : 4,411,268
DATED : October 25, 1983
INVENTOR(S) : James A. Cox

It is certified that error appears in the above-identified patent and that said Letters Patent are hereby corrected as shown below:

Column 5, line 24, the word "of" should be deleted.

Column 6, line 47, the word appearing as "details" should read --detail--.

Signed and Sealed this

Twenty-first Day of February 1984

[SEAL]

Attest:

GERALD J. MOSSINGHOFF

Attesting Officer    Commissioner of Patents and Trademarks